(12) United States Patent
Smith et al.

(10) Patent No.: US 12,085,546 B2
(45) Date of Patent: Sep. 10, 2024

(54) METHOD AND SYSTEM OF IGNITION INTERLOCK DEVICE CALIBRATION AND CLEANING

(71) Applicant: Consumer Safety Technology LLC, Des Moines, IA (US)

(72) Inventors: David L. Smith, Des Moines, IA (US); Kevin Kauffold, Des Moines, IA (US); Michael White, Des Moines, IA (US); James Thomsen, Des Moines, IA (US); Elizabeth Youngwirth, Des Moines, IA (US)

(73) Assignee: Consumer Safety Technology, LLC, Des Moines, IA (US)

( * ) Notice: Subject to any disclaimer, the term of this patent is extended or adjusted under 35 U.S.C. 154(b) by 431 days.

(21) Appl. No.: 17/321,021

(22) Filed: May 14, 2021

(65) Prior Publication Data
US 2022/0365050 A1 Nov. 17, 2022

(51) Int. Cl.
*G01N 33/00* (2006.01)
*A61L 2/10* (2006.01)
*A61L 2/20* (2006.01)
*B60K 28/06* (2006.01)
*G01N 33/497* (2006.01)
(Continued)

(52) U.S. Cl.
CPC ....... *G01N 33/0029* (2013.01); *B60K 28/063* (2013.01); *G01N 33/0006* (2013.01); *G01N 33/4972* (2013.01); *A61L 2/10* (2013.01); *A61L 2/202* (2013.01)

(58) Field of Classification Search
CPC ...... B60K 28/063; B60K 28/06; B60K 28/02; B60K 2028/003; G01N 33/4972; G01N 33/497; G01N 33/98; G01N 33/0006; G01N 2001/2244; B60W 2540/24; B60W 2040/0836; B60W 40/08; A61B 5/082; A61B 5/18; A61B 5/4845; A61B 2010/0009; A61B 2010/0087; A61B 2560/0431; A61B 5/6893; A61B 5/097; A61B 5/083; A61B 5/0833; A61B 5/0836;
(Continued)

(56) References Cited

U.S. PATENT DOCUMENTS 5,426,415 A 6/1995 Prachar et al.
6,167,746 B1 1/2001 Gammenthaler
(Continued)

FOREIGN PATENT DOCUMENTS

CA 2366341 5/2010

OTHER PUBLICATIONS

"How Can I Clean My Alcolizer Instruments?", https://www.alcolizer.com/faq/can-clean-alcolizer-instruments/, (2 pages) at least as early as Feb. 8, 2022.
(Continued)

*Primary Examiner* — Peter J Macchiarolo
*Assistant Examiner* — Anthony W Megna Fuentes
(74) *Attorney, Agent, or Firm* — Pauly, DeVries Smith & Deffner LLC (57) ABSTRACT

A system and method of bio-cleaning an ignition interlock device (IID). The method comprises receiving a handheld unit of an IID in a fixtured arrangement with an IID calibration station, and applying, while maintaining the IID handheld unit in the fixtured arrangement, a bio-cleaning agent to at least one ingress port of the IID handheld unit in a consolidated IID bio-cleaning and IID calibration operation.

20 Claims, 4 Drawing Sheets

(51) Int. Cl.
*A61L 2/07* (2006.01)
*A61L 2/22* (2006.01)

(58) Field of Classification Search
CPC . A61L 2/00; A61L 2/0094; A61L 2/07; A61L 2/10; A61L 2/20; A61L 2/202
See application file for complete search history.

(56) References Cited

U.S. PATENT DOCUMENTS

| | | |
|---|---|---|
| 6,853,956 B2 | 2/2005 | Ballard et al. |
| 6,956,484 B2 | 10/2005 | Crespo et al. |
| 7,135,788 B2 | 11/2006 | Metlitzky et al. |
| 8,078,334 B2 | 12/2011 | Goodrich |
| 8,957,771 B2 | 2/2015 | Arringdale et al. |
| 9,442,103 B1 | 9/2016 | Goad |
| 9,481,245 B2 | 11/2016 | Nelson et al. |
| 9,562,883 B2 | 2/2017 | Silverman et al. |
| 9,772,318 B1 | 9/2017 | Lyon |
| 9,908,488 B2 | 3/2018 | Shafer |
| 10,436,770 B2 | 10/2019 | Lyon |
| 10,458,975 B1 | 10/2019 | Lyon |
| 10,663,440 B2 | 5/2020 | DeVries |
| 10,877,008 B2 | 12/2020 | DeVries |
| 10,919,389 B2 | 2/2021 | DeVries et al. |
| 11,047,840 B2 | 6/2021 | DeVries et al. |
| 2015/0197151 A1 | 7/2015 | Ballard |
| 2015/0244452 A1 | 8/2015 | Wojciech et al. |
| 2016/0086021 A1 | 3/2016 | Grohman et al. |
| 2017/0282713 A1 | 10/2017 | DeVries et al. |
| 2017/0313189 A1 | 11/2017 | Walter et al. |
| 2018/0011068 A1 | 1/2018 | Lyon |
| 2018/0209955 A1 | 7/2018 | Moeller |
| 2019/0246958 A1 | 8/2019 | Moeller et al. |
| 2019/0376949 A1 | 12/2019 | Lyon |
| 2020/0361314 A1 | 11/2020 | Ringgenberg et al. |
| 2021/0148892 A1 | 5/2021 | Ruland et al. |
| 2021/0156834 A1 | 5/2021 | DeVries et al. |
| 2022/0142585 A1 | 5/2022 | Williams |
| 2022/0142586 A1 | 5/2022 | Williams |
| 2022/0315008 A1 | 10/2022 | Smith et al. |
| 2023/0022836 A1 | 1/2023 | Smith et al. |
| 2023/0028690 A1 | 1/2023 | Woods et al. |

OTHER PUBLICATIONS

"How Should I Clean My Alcohawk?", https://www.breathalyzers.com/index.php/alcohawk/blog/how-should-i-clean-my-alcohawk/ (2 pages) at least as early as Feb. 8, 2022.

"How to Clean Your Interlock," https://draegerinterlock.com/ignition-interlock-devices/blog/how-to-clean-your-interlock-device/#:~:text=%20How%20to%20Clean%20Your%20Interlock%20Device%20,most%20crucial%20aspects%20of%20cleaning%20an...%20More%20, (2 pgs) as least as early as Feb. 8, 2022.

"What to Know About Ignition Intoxalock Device Hygiene and Steps During a Virus Outbreak," https://www.intoxalock.com/blog/post/ignition-interlock-device-sanitation/, (2 pages) at least as early as Feb. 8, 2022.

> Receiving a handheld unit of an ignition interlock device (IID) in a fixtured arrangement with an IID calibration station
> 310

> Applying, while maintaining the handheld unit in the fixtured arrangement, a bio-cleaning agent to at least one ingress port of the handheld unit.
> 320

Receiving a handheld unit of an ignition interlock device (IID) in a fixtured arrangement with an IID calibration station
410

Initiating a calibration process that indicates operational suitability of the IID based upon an impairment parameter determined in accordance with a fuel cell sensor device of the handheld unit.
420

Applying, upon maintaining the handheld unit in the fixtured arrangement, a bio-cleaning agent to at least one ingress port of the handheld unit.
430

FIG. 4

METHOD AND SYSTEM OF IGNITION INTERLOCK DEVICE CALIBRATION AND CLEANING

TECHNICAL FIELD

The disclosure herein relates to vehicle ignition interlock systems and methods of calibration and cleaning thereof.

BACKGROUND

Vehicles can incorporate a breath alcohol ignition interlock device (IID) to prevent a driver from operating a vehicle while intoxicated with alcohol. Such devices are designed to prevent a driver from starting a motor vehicle when the driver's impairment level, such a breath alcohol content (BrAC), is at or above a mandated alcohol concentration threshold. Various jurisdictions have adopted a law providing for use of such IID devices as a sanction for drivers convicted of driving while intoxicated, or as a condition of restoring driving privileges during some probationary period after such offenses. A typical IID device meets guidelines established by the National Highway Traffic Safety Administration (NHTSA) in published model specifications for IIDs, which specify various tests that such a device must pass to make it an effective and reliable deterrent to intoxicated driving.

In deployment of an IID, vehicle operators subject to sanction are required to have their installed IID periodically calibrated at a state-approved vehicle IID service center, typically every 3 or 4 months, for operational accuracy to ensure integrity of operator impairment measurements.

DETAILED DESCRIPTION

Embodiments herein recognize that IID devices requiring a user's breath sample during which the user's mouth comes into regular contact need to be safe from contaminants, both inorganic and biological contaminants. Among other benefits and technical effects, embodiments herein provide a method and system of efficiently performing a bio-cleaning operation in conjunction with every periodic IID calibration operation prior to re-deployment of an IID.

In deploying embodiments described herein, a record of bio-cleaning can automatically be associated with the record of the IID calibration, thus eliminating the need for tracking and communicating two separate operations, each of which can be considered essential for successful re-deployment of the IID. Such consolidated tracking and reporting of separate bio-cleaning and calibration operations efficiently minimizes computer processor cycles for data records accessing or storage as well as less memory storage capacity as compared with that required for separate tracking and reporting of same. Yet further, embodiments herein provide for accomplishing bio-cleaning of the IID during a same fixturing step when the IID is fixed into place in a calibration station for purposes of calibrating the IID, and in a manner that minimizes the amount of manual handling and manual steps required to accomplish both the bio-cleaning and calibration operations. IID tracking via a consolidated data record that ties both the calibration and bio-cleaning operations also enables simplified, efficient storage and retrieval of IID and IID user data records, and enhances the integrity of said operations.

Provided is a method of bio-cleaning an ignition interlock device (IID). The method comprises receiving a handheld unit of an IID in a fixtured arrangement with IID calibration station, and applying, while maintaining the handheld unit in the fixtured arrangement, a bio-cleaning agent to at least one ingress port of the handheld unit.

As used herein, the term bio-cleaning means cleaning the IID handheld unit using anti-viral, anti-bacterial or disinfecting agents, rather than, or in addition to, simply cleaning to remove dust and surface contaminants for cosmetic effects.

Also provided is an ignition interlock device (IID) calibration station having a processor and a non-transitory memory including instructions. The instructions when executed in the processor cause operations comprising detecting placement of a handheld unit of an IID device in fixtured arrangement within the IID calibration station; and generating, at a display interface of at least one of the handheld unit and the IID calibration station, an instruction associated with application of a bio-cleaning agent to an ingress port of the handheld unit.

Further provided is a non-transitory computer readable memory storing instructions executable in a processor device. The instructions when executed in the processor cause operations comprising detecting placement of a handheld unit of an IID device in fixtured arrangement within the IID calibration station; and generating, at a display interface of at least one of the handheld unit and the IID calibration station, an instruction associated with application of a bio-cleaning agent to an ingress port of the handheld unit.

Embodiments described herein can be implemented using programmatic modules, through the use of instructions that are executable by one or more processors. A programmatic module can include a program, a sub-routine, a portion of a program, or a software component or a hardware component capable of performing one or more stated tasks or functions. As used herein, a programmatic module can exist on a hardware component independently of other modules or components, or can be a shared element of other modules, programs or machines.

Some embodiments of IID's and IID calibration stations described herein can generally incorporate computing and communication resources, such as processor and memory resources. Memory, processing, and network resources, local or remote but communicatively accessible, may be applied in connection with the establishment, use, or performance of any embodiment described herein, including with the performance of any method or with the implementation of any system.

One or more embodiments described herein provide that methods, techniques, and actions performed in an IID calibration station are performed programmatically, or as a computer-implemented method. Programmatically, as used herein, means through the use of code or computer-executable instructions. These instructions can be stored in one or more memory resources accessible to the IID calibration station and to the IID handheld unit.

Device and System

Figure 1:
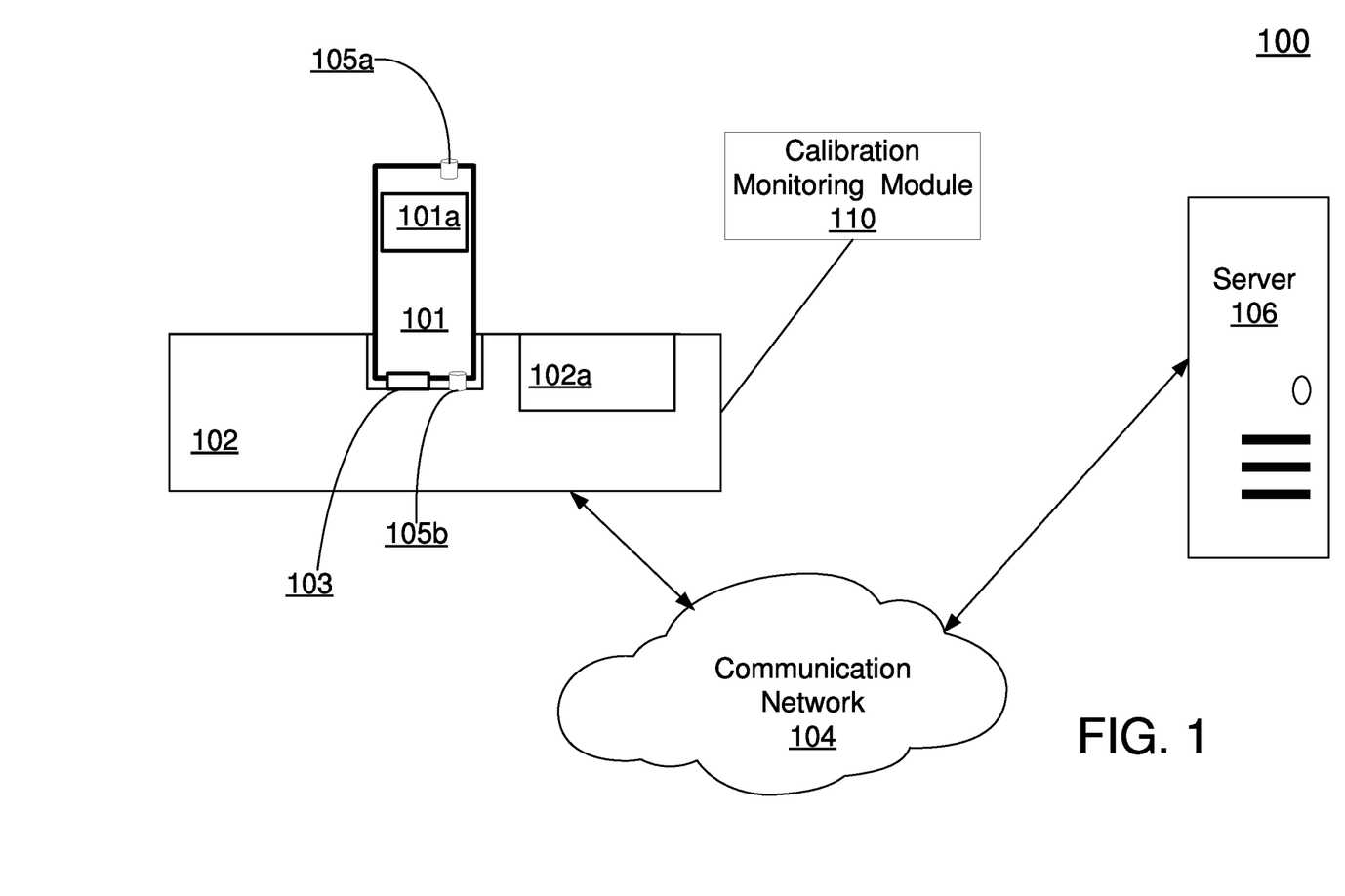
FIG. 1 illustrates, in an example embodiment, a vehicle IID calibration station system.

FIG. 1 illustrates, in an example embodiment, vehicle IID calibration and cleaning system 100 within a computing and communication network system. IID handheld unit 101 includes a processor and a memory. The memory stores executable instructions, constituting calibration monitoring module 110 for deploying IID handheld unit 101 in conjunction with IID calibration station 102 and calibration monitoring server computing device 106 via communication network 104. In variations, some portions, or all, of the executable instructions constituting calibration monitoring module 110 may be hosted at calibration monitoring calibration monitoring server computing device 106 in communication with IID handheld unit 101 via communication network 104. Calibration monitoring module 110 includes logic related to storing vehicle and IID driver account details in conjunction with IID calibration and cleaning service operations. In some variations, calibration and cleaning operations as monitored via calibration monitoring server 106 can be managed and maintained in deployment by an IID services provider, and allows reporting of driver and related IID calibration and cleaning operations history to state authorities. In some embodiments herein, breath alcohol content (BrAC) measurements associated with a user breath sample received at a mouthpiece, or ingress ports 105a, 105b, of IID handheld unit 101 can be correlated with blood alcohol content (BAC) levels, It is contemplated that, in alternate embodiments, portions of the logic constituting calibration monitoring module 110 for deploying IID handheld unit 101 in conjunction with IID calibration station 102 can be stored at calibration monitoring server computing device 106 via communication network 104

In one particular embodiment of IID 105 as depicted in FIG. 1, IID handheld unit 101 can include display interface 102a, which may be an LED display screen in one embodiment. IID calibration station 102 can include display interface 101a, such as an LED display screen in one embodiment, suitable for displaying instructions or process status related to IID calibration and cleaning operations to an operator of IID calibration station 102. In prelude to the calibrations and bio-cleaning processes described herein, IID handheld unit 101 may be mechanically and electrically fixtured into place within IID calibration station 102 via connector 103 implemented in mating counterpart connector components.

Figure 2:
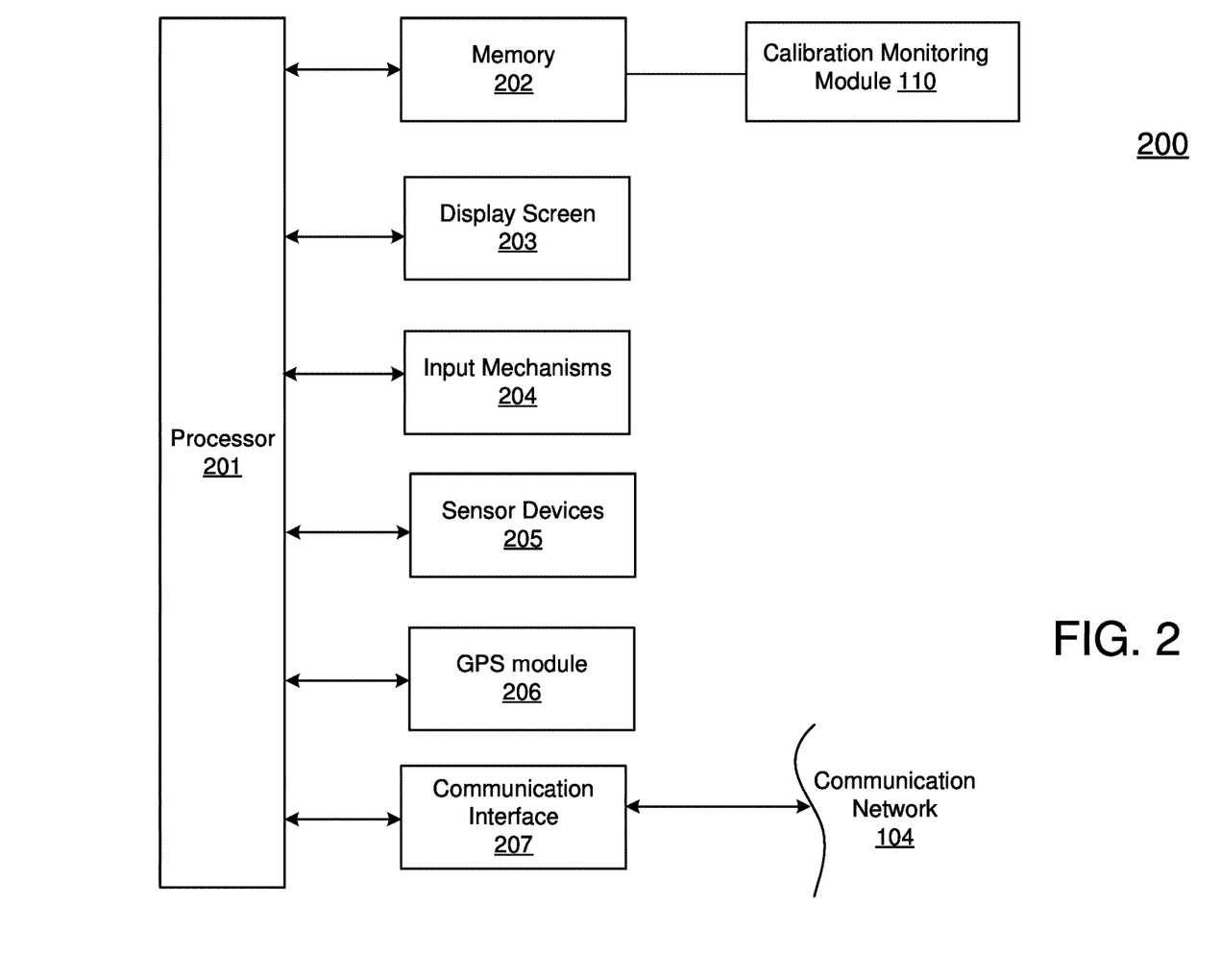
FIG. 2 illustrates, in one embodiment, an example architecture of a vehicle IID calibration station system within a computing and communication network.

FIG. 2 illustrates, in one embodiment, example architecture 200 of a vehicle IID calibration and cleaning system within a computing and communication system. In one embodiment, IID handheld unit 101 can include input mechanisms 204 such as resistive- or capacitance-based input mechanisms or software-implemented touchscreen input functionality, display screen 203, audible alerts capability, and sensor devices 205. Input mechanisms 204 may also include ingress ports 105a, 105b to receive orally delivered breath samples at IID handheld unit 101, submitted by a vehicle user or driver. IID handheld unit 101 may also include capability for detecting and communicatively accessing wireless communication signals, including but not limited to any of Bluetooth, Wi-Fi, RFID, and global positioning system (GPS) signals, and incorporate communication interface 207 for communicatively coupling to communication network 104, such as by sending and receiving cellular and GPS data over data channels and voice channels. IID handheld unit 101, in some embodiments, can incorporate GPS module 206 that includes GPS receiver and transmitter circuitry for accessing and enabling GPS signals and data.

Sensor devices 205 of IID handheld unit 101 can include an alcohol fuel cell sensor. Breath alcohol testing and monitoring devices are operated by a user blowing into ingress port 105a, 105b in conjunction with a fuel cell sensor that measures alcohol content of the driver's breath, thereby providing an objective representation or estimate of the blood alcohol concentration of the driver's bloodstream. An electrical signal generated from the fuel cell, or similar alcohol-sensing element is used to determine an operator's breath alcohol content. If the operator's breath alcohol content does not exceed a predetermined threshold, the operator is determined as not intoxicated or impaired. If the breath sample delivered from the user registers a higher breath alcohol content than the predetermined allowable threshold, IID handheld unit 101 generates, records and reports an impaired driving violation.

Calibration monitoring module 110 can be constituted of computer processor-executable code stored in memory 202 of IID calibration station 102 or, in some embodiments, in IID handheld unit 101 for deploying functionality ascribed to embodiments herein. In one variation, calibration monitoring module 110 may be stored in memory 202 IID calibration station 102 upon accessing and downloading, via communication network 104, from calibration monitoring calibration monitoring server computing device 106 or other remote server.

In particular embodiments, calibration monitoring module 110 includes instructions executable in processor 210 to electrically detect placement of IID handheld unit 101 into a fixtured arrangement within IID calibration station 102.

In embodiments, the fixtured arrangement comprises establishing at least one of an electrical connection and a mechanical connection between the IID handheld unit and the calibration station. Complementary male-female mating counterparts constituting connector 103 can be used to establish electro-mechanical connection, or fixturing, between IID handheld unit 101 and calibration station 102. In some embodiments, the electro-mechanical connection via connector 103 between IID handheld unit 101 and calibration station 102 may employ spring loaded pins, also referred to as pogo pins, to establish a robust mechanical connection while also providing an electrical communication path.

In some embodiments, the ingress port can be either, or both, of a top port 105a and a bottom port 105b located on an external housing of IID handheld unit 101. The method further comprises applying the bio-cleaning agent into a breath sample channel within the handheld unit, the breath sample channel providing a flow path for passage of breath sample air between ingress port 105a, 105b and a fuel cell sensor device located within the housing.

Calibration monitoring module 110 further includes executable instructions to generate, at a display interface 101a of IID handheld unit 101 or in other variations, display interface 102a of the IID calibration station 102, an instruction associated with application of a bio-cleaning agent to an ingress port of the handheld unit. The instruction may specify a number of steps and materials or agents for the bio-cleaning operation and also an order of steps associated therewith, facilitating thorough bio-cleaning of the IID handheld unit to be accomplished in a detailed and standardized or structured manner.

In some embodiments, the bio-cleaning agent comprises at least one of an anti-viral and an anti-bacterial cleaning agent. In embodiments, the anti-viral and the anti-bacterial cleaning agent applied can be one or more of a biomist, an ultra-violet (UV) light guide probe, and a bio-cleaning fluid.

In an embodiment, UVC light, which is the shortest wavelength of the three forms (UVA, UVB, UVC) of UV, is applied as a germicidal agent by way of germicidal UV-C lighting, in one embodiment. A UVC light guide probe can be retractably deployed to provides UVC light along a set of contiguous portions in any length of the breath sample channel extending from ingress port 105a, 105b to a fuel cell sensor of IID handheld unit 101, the UV light being typically provided at a frequency range of between the wavelengths of 207 and 222 nanometers.

In embodiments, the biomist applied via ingress port 105a, 105b can include antiviral, disinfectant and germicidal cleaning mists. In some variations, the biomist can be applied to external surfaces by lowering an enclosure or cover completely around IID handheld unit 101 in a contained space while fixtured within calibration station 102 and applying the biomist to effectively blanket the external surfaces. In some examples, the biomist can include steam or ozone, including pressurized deployments thereof. In other variations, it is contemplated also that disinfecting or antiviral solutions, for instance ethyl alcohol and isopropyl alcohol in some examples, included diluted versions thereof, can be applied to IID handheld unit 101, whether to external surfaces or to the breath sample channel via ingress port 105a, 105b. In some variations, the biomist can include gaseous versions of, or containing, any of the disinfecting, antiviral or antibacterial agents described herein such as an alcohol vapor containing ethyl and isopropyl alcohol.

In some variations, the method further comprises initiating, at one of prior to and subsequent to applying the bio-cleaning agent, a calibration process that indicates operational suitability of the IID based on an impairment parameter determined in accordance with a fuel cell sensor device of the handheld unit. The fuel cell sensor can be an alcohol fuel cell sensor, in an embodiment where the impairment parameter comprises a breath alcohol content (BrAC), intended to serve as a proxy for a blood alcohol content of a user that orally provides a breath sample at ingress port 105a, 105b.

Methodology

Figure 3:
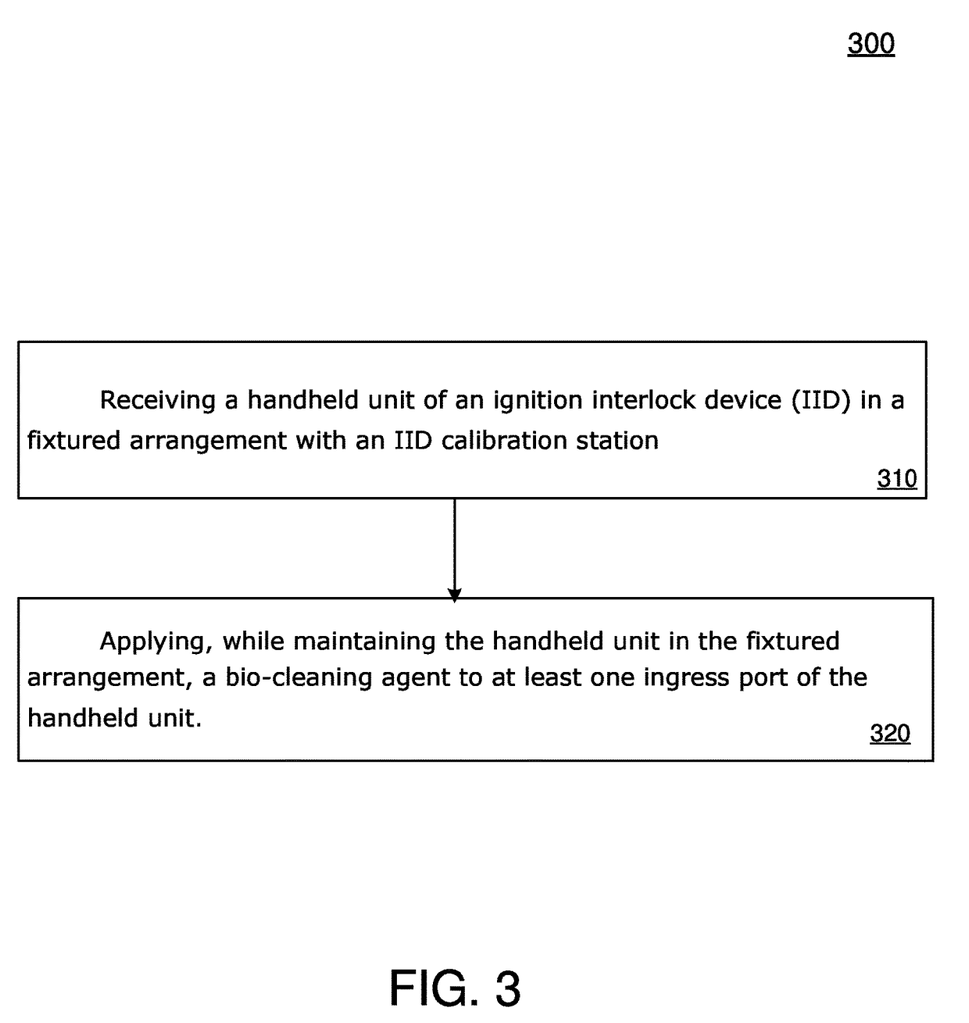
FIG. 3 illustrates, in an example embodiment, a method of cleaning an IID handheld unit in conjunction with a vehicle IID calibration station system.

FIG. 3 illustrates, in an example embodiment, method 300 of cleaning a handheld unit of a vehicle IID within vehicle IID calibration system. Examples of method steps described herein are related to deployment and use of IID handheld unit 101 as described herein. According to one embodiment, the techniques are performed in processor 201 executing one or more sequences of software logic instructions that constitute calibration monitoring module 110 of IID handheld unit 101. In embodiments, calibration monitoring module 110 may be remotely hosted at calibration monitoring calibration monitoring server computing device 106 and is communicatively coupled with IID handheld unit 101. Such instructions may be read into memory 202 from machine-readable medium, such as memory storage devices. Executing the instructions of calibration monitoring module 110 stored in memory 202 causes processor 201 to perform the process steps described herein. In alternative implementations, at least some hard-wired circuitry may be used in place of, or in combination with, the software logic instructions to implement examples described herein. Thus, the examples described herein are not limited to any particular combination of hardware circuitry and software instructions.

At step 310, receiving, in a fixtured arrangement within IID calibration station 102, a IID handheld unit 101.

In embodiments, the fixtured arrangement comprises establishing at least one of an electrical connection and a mechanical connection between the IID handheld unit and the calibration station. Complementary male-female mating counterparts constituting connector 103 can be used to establish electro-mechanical connection, or fixturing, between IID handheld unit 101 and calibration station 102. In some embodiments, the electro-mechanical connection via connector 103 between IID handheld unit 101 and calibration station 102 may employ spring loaded pins, also referred to as pogo pins, to establish a robust mechanical connection while also providing an electrical communication path.

At step 320, upon maintaining IID handheld unit 101 in the fixtured arrangement, applying a bio-cleaning agent to at least one ingress port 105a, 105b of IID handheld unit 101.

In some embodiments, the ingress port can be either, or both, of a top port 105a and a bottom port 105b located on an external housing of IID handheld unit 101. The method further comprises applying the bio-cleaning agent into a breath sample channel within the handheld unit, the breath sample channel providing a flow path for passage of breath sample air between ingress port 105a, 105b and a fuel cell sensor device located within the housing.

In some embodiments, the bio-cleaning agent comprises at least one of an anti-viral and an anti-bacterial cleaning agent. In embodiments, the anti-viral and the anti-bacterial cleaning agent applied can be one or more of a biomist, an ultra-violet (UV) light guide probe, and a bio-cleaning fluid.

In an embodiment, UVC light, which is the shortest wavelength of the three forms (UVA, UVB, UVC) of UV, is applied as a germicidal agent by way of germicidal UV-C lighting, in one embodiment. A UVC light guide probe can be retractably deployed to provides UVC light along a set of contiguous portions in any length of the breath sample channel extending from ingress port 105a, 105b to a fuel cell sensor of IID handheld unit 101, the UV light being typically provided at a frequency range of between the wavelengths of 207 and 222 nanometers.

In embodiments, the biomist applied via ingress port 105a, 105b can include antiviral, disinfectant and germicidal cleaning mists. In some variations, the biomist can be applied to external surfaces by lowering an enclosure or cover completely around IID handheld unit 101 in a contained space while fixtured within calibration station 102 and applying the biomist to effectively blanket the external surfaces. In some examples, the biomist can include steam or ozone, including pressurized deployments thereof. In other variations, it is contemplated also that disinfecting or antiviral solutions, for instance ethyl alcohol and isopropyl alcohol in some examples, included diluted versions thereof, can be applied to IID handheld unit 101, whether to external surfaces or to the breath sample channel via ingress port 105a, 105b. In some variations, the biomist can include gaseous versions of, or containing, any of the disinfecting, antiviral or antibacterial agents described herein such as an alcohol vapor containing ethyl and isopropyl alcohol.

In some variations, the method further comprises initiating, at one of prior to and subsequent to applying the bio-cleaning agent, a calibration process that indicates operational suitability of the IID based on an impairment parameter determined in accordance with a fuel cell sensor device of the handheld unit. The fuel cell sensor can be an alcohol fuel cell sensor, in an embodiment where the impairment parameter comprises a breath alcohol content (BrAC), intended to serve as a proxy for a blood alcohol content of a user that orally provides a breath sample at ingress port 105a, 105b.

In embodiments, IID calibration station 102 is communicatively connected with a calibration monitoring server computing device 106. Upon completing the bio-cleaning operation and the calibration operation, a timestamp indicating time of completion of one or both of bio-cleaning and IID calibration operations in conjunction with a unique identifier associated with the IID can be communicated to calibration monitoring server computing device 106. The unique identifier may be associated with a named IID customer account or IID end user party, and also a particular vehicle into which the IID is installed and registered for use. In this manner, a record of bio-cleaning can be automatically associated with a record of the IID calibration, thus eliminating the need for tracking and communicating two separate operations, each of which can be considered essential for successful re-deployment of the IID. Among other administrative benefits, such consolidated tracking and reporting of separate operations efficiently minimizes computer processor and memory storage cycles as compared with that required for separate tracking and reporting of same.

Figure 4:
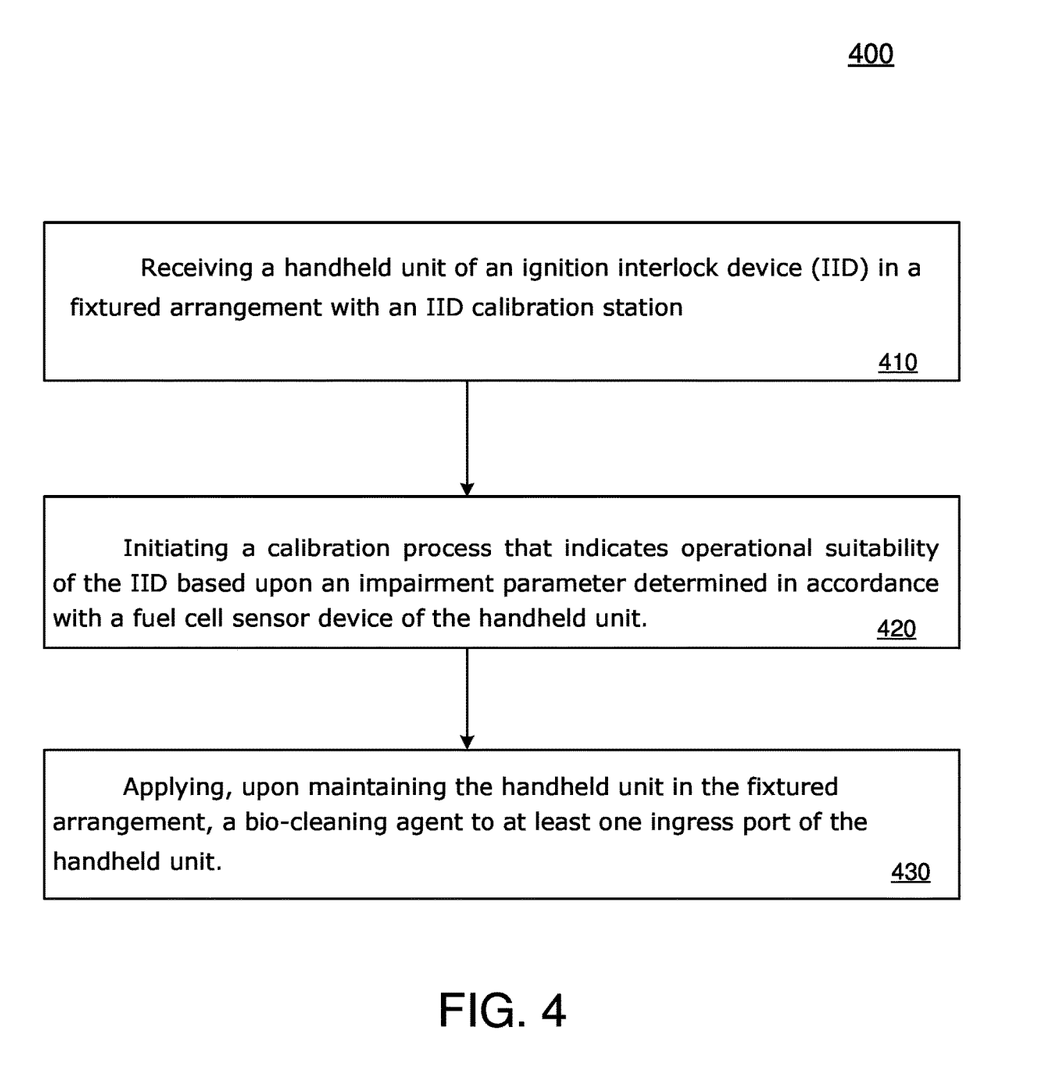
FIG. 4 illustrates, in a further example embodiment, a method of cleaning an IID handheld unit in conjunction with a vehicle IID calibration station system.

FIG. 4 illustrates, in a further example embodiment, method 400 of cleaning an IID handheld unit in conjunction with a vehicle IID calibration station system. In the example illustrated in FIG. 4, steps as described with reference to FIG. 3 may be incorporated into the technique of FIG. 4. In particular, one or more steps of the IID calibration process may be integrated or combined with one or more steps of the IID bio-cleaning process of FIG. 3.

At step 410, receiving, in a fixtured arrangement within IID calibration station 102, a IID handheld unit 101.

At step 420, initiating an IID calibration process that indicates operational suitability of the IID based upon an impairment parameter determined in accordance with a fuel cell sensor device of the handheld unit. In some embodiments, the impairment parameter is representative of a breath alcohol content as embodied in a IID user's breath sample, measured using an alcohol fuel cell sensor component within IID handheld unit 101.

At step 430, applying, responsive to maintaining IID handheld unit 101 in the fixtured arrangement, a bio-cleaning agent to at least one ingress port of IID handheld unit 101.

In yet other variations, it is contemplated that the IID calibration process can be performed subsequent to applying the bio-cleaning agent to IID handheld unit 101.

It is contemplated for embodiments described herein to extend to individual elements and concepts described herein, independently of other concepts, ideas or system, as well as for embodiments to include combinations of elements recited anywhere in this application. For example, although techniques of anti-circumvention monitoring described herein are disclosed in context of alcohol sensor devices and alcohol impaired driving, it is contemplated that such techniques, in conjunction with appropriate, respective sensor devices, be applied to alternate intoxicant agents that result in impaired driving. Such intoxicants can include, but not necessarily be limited to, drugs including cannabinoids, opiates, and methamphetamines.

Although embodiments are described in detail herein with reference to the accompanying drawings, it is contemplated that the disclosure herein is not limited to only such literal embodiments. As such, many modifications including variations in sequence of the method steps in conjunction with varying combinations of user interface features disclosed herein will be apparent to practitioners skilled in this art. Accordingly, it is intended that the scope of the invention be defined by the following claims and their equivalents. Furthermore, it is contemplated that a particular feature described either individually or as part of an embodiment can be combined with other individually described features, or parts of other embodiments. Thus, the absence of describing combinations of such do not preclude the inventor from claiming rights to such combinations.

What is claimed is:

1. A method of cleaning an ignition interlock device (IID) comprising:
   receiving, in a fixtured arrangement within an IID calibration station, an IID handheld unit; and
   applying, responsive to maintaining the IID handheld unit in the fixtured arrangement, a bio-cleaning agent to at least one ingress port of the IID handheld unit; wherein the bio-cleaning agent comprises a UV light guide probe.

2. The method of claim 1, wherein the fixtured arrangement comprises establishing at least one of an electrical connection and a mechanical connection between the IID handheld unit and the IID calibration station.

3. The method of claim 2, further comprising initiating, at one of prior to and subsequent to applying the bio-cleaning agent, a calibration process that indicates operational suitability of the IID based on an impairment parameter determined in accordance with a fuel cell sensor device of the IID handheld unit.

4. The method of claim 3, wherein the impairment parameter comprises a breath alcohol content (BrAC).

5. The method of claim 1, wherein the ingress port comprises one of a top and a bottom port of a housing of the IID handheld unit, the method further comprising applying the bio-cleaning agent into a breath sample channel within the IID handheld unit, the breath sample channel configured for fluid communication between the ingress port and a fuel cell sensor device located within the housing.

6. The method of claim 5, wherein the bio-cleaning agent comprises at least one of an anti-viral and an anti-bacterial cleaning agent.

7. The method of claim 6, wherein the at least one of the anti-viral and the anti-bacterial cleaning agent comprises at least one of: a biomist, and a bio-cleaning fluid.

8. The method of claim 7, wherein the biomist comprises at least one of ozone vapor, steam and an alcohol vapor.

9. The method of claim 1, wherein the UV light guide probe retractably provides UV light along a set of contiguous portions of the breath sample channel, the UV light being provided at a frequency range of the UV light being typically provided at a frequency range between the wavelengths of 207 and 222 nanometers.

10. The method of claim 1, wherein the IID calibration station is communicatively connected with a server computing device, the method further comprising communicating a timestamp of a completed bio-cleaning operation in conjunction with a unique identifier associated with the IID to the server computing device.

11. An ignition interlock device (IID) calibration station comprising:
   a processor; and
   a non-transitory memory including instructions, the instructions when executed in the processor causing operations comprising:
   detecting placement of an IID handheld unit in fixtured arrangement within the IID calibration station; and generating, at a display interface of at least one of the IID handheld unit and the IID calibration station, an instruction associated with application of a bio-cleaning agent to an ingress port of the IID handheld unit; wherein the bio-cleaning agent comprises a UV light guide probe.

12. The ignition interlock device (IID) calibration station of claim 11, wherein the fixtured arrangement comprises establishing at least one of an electrical connection and a mechanical connection between the IID handheld unit and the IID calibration station.

13. The ignition interlock device (IID) calibration station of claim 12, further comprising instructions executable to cause initiating, at one of prior to and subsequent to applying the bio-cleaning agent, a calibration process that indicates operational suitability of the IID based on an impairment parameter determined in accordance with a fuel cell sensor device of the IID handheld unit.

14. The ignition interlock device (IID) calibration station of claim 13, wherein the impairment parameter comprises a breath alcohol content (BrAC).

15. The ignition interlock device (IID) calibration station of claim 11, wherein the ingress port comprises one of a top and a bottom port of a housing of the IID handheld unit, and further comprising instructions executable to cause initiating applying the bio-cleaning agent into a breath sample channel within the IID handheld unit, the breath sample channel configured for fluid communication between the ingress port and a fuel cell sensor device located within the housing.

16. The ignition interlock device (IID) calibration station of claim 15, wherein the bio-cleaning agent comprises at least one of an anti-viral and an anti-bacterial cleaning agent.

17. The ignition interlock device (IID) calibration station of claim 16, wherein the at least one of the anti-viral and the anti-bacterial cleaning agent comprises at least one of: a biomist and a bio-cleaning fluid.

18. The ignition interlock device (IID) calibration station of claim 11, wherein the UV light guide probe retractably provides UV light along a set of contiguous portions of the breath sample channel, the UV light being provided at a frequency range of between the wavelengths of 207 and 222 nanometers.

19. The ignition interlock device (IID) calibration station of claim 11, wherein the IID calibration station is communicatively connected with a server computing device, and further comprising instructions executable to cause communicating a timestamp of a completed bio-cleaning operation in conjunction with a unique identifier associated with the IID to the server computing device.

20. A non-transitory computer readable memory storing instructions executable in a processor device, wherein the instructions, when executed by the processor device, cause the processor device to perform operations comprising:
  detecting placement of an IID handheld unit in fixtured arrangement within an IID calibration station; and
  generating, at a display interface of at least one of the IID handheld unit and the IID calibration station, an instruction associated with application of a bio-cleaning agent to an ingress port of the IID handheld unit; wherein the bio-cleaning agent comprises a UV light guide probe.

* * * * *